United States Patent [19]

Reuss et al.

[11] Patent Number: 4,664,665
[45] Date of Patent: May 12, 1987

[54] INTRAOCULAR LENS WITH FOLDABLE SIDES

[75] Inventors: Gerald Reuss, Richfield; Kevin Gwash, Big Lake; Charles Gay, Bloomington; Noel G. Bissonette, Richfield, all of Minn.

[73] Assignee: Precision-Cosmet Co., Inc., Minnetonka, Minn.

[21] Appl. No.: 838,907

[22] Filed: Mar. 12, 1986

Related U.S. Application Data

[63] Continuation-in-part of Ser. No. 677,753, Dec. 3, 1984, abandoned.

[51] Int. Cl.⁴ .............................................. A61F 2/16
[52] U.S. Cl. ....................................................... 623/6
[58] Field of Search ............................................. 623/6

[56] References Cited

U.S. PATENT DOCUMENTS 4,605,409 8/1986 Kelman ................................. 623/6

FOREIGN PATENT DOCUMENTS 0099641 2/1984 European Pat. Off. ................ 623/6

Primary Examiner—Richard J. Apley
Assistant Examiner—James Prizant
Attorney, Agent, or Firm—Merchant, Gould, Smith, Edell, Welter & Schmidt

[57] ABSTRACT

The present invention is directed to an intraocular lens having a lens body which includes a primary portion and secondary portions. The secondary portions are connected to the primary portion with connect members. The secondary portions may be folded with respect to the primary portion so that a smaller perimeter for the lens body is possible during lens insertion into the eye thereby requiring a smaller incision in the cornea than is otherwise possible.

6 Claims, 11 Drawing Figures

FIG. 6
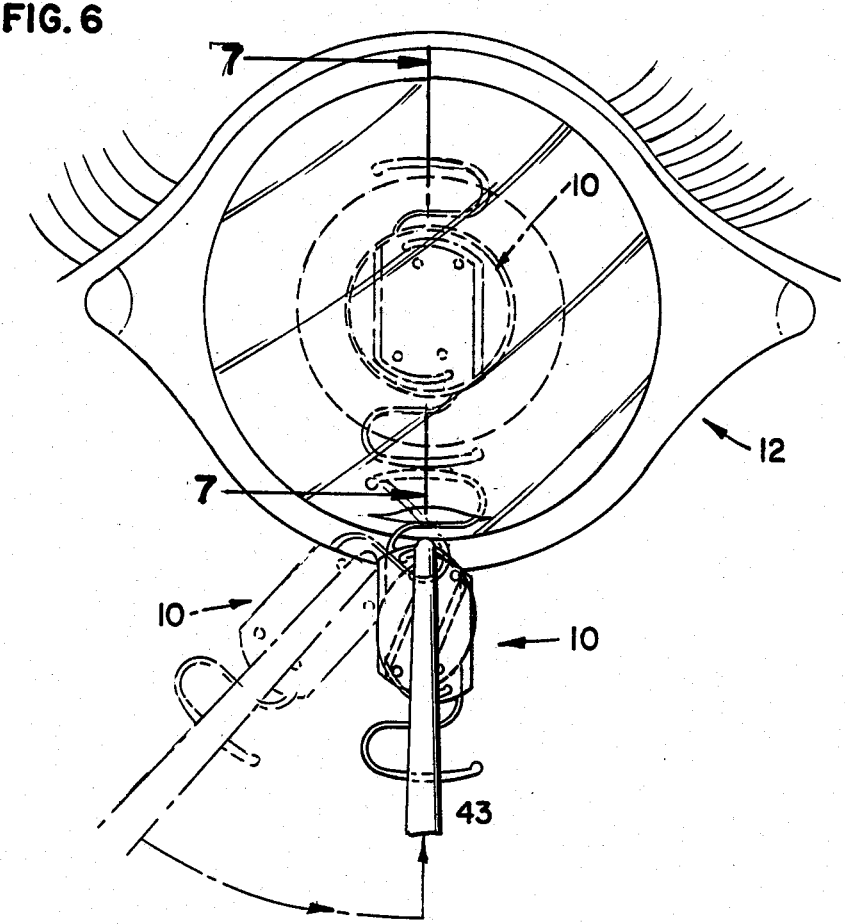
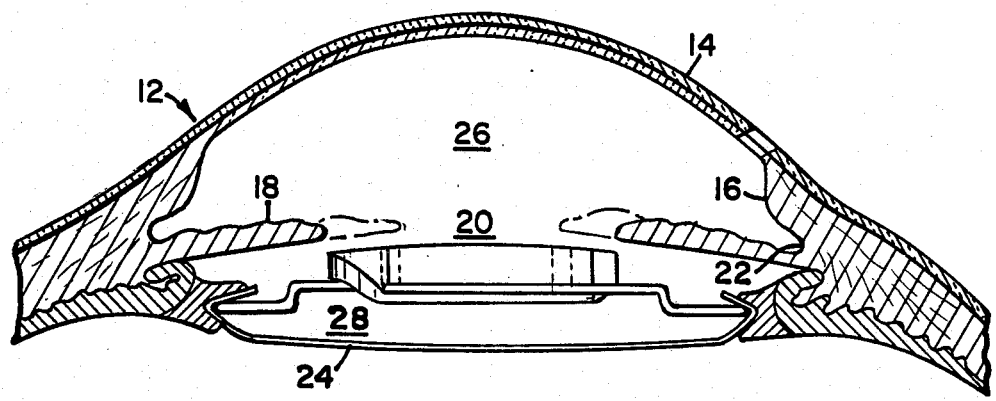
FIG. 7

INTRAOCULAR LENS WITH FOLDABLE SIDES

This is a continuation-in-part application of Ser. No. 677,753, filed Dec. 3, 1984, now abandoned.

FIELD OF THE INVENTION

The present invention is directed to an intraocular lens of a type having foldable sides so that the width of the lens during insertion in the eye may be made smaller than the width when implanted, thereby requiring a smaller incision in the cornea than is now the case for implantation.

BACKGROUND OF THE INVENTION

Many different types of synthetic intraocular lens structures have been developed to replace the natural lens of the human eye after lens removal during cataract surgery. In such operations, an opening or incision is made in the cornea and in the anterior surface of the capsular bag, commonly in the area adjacent to the pupillary aperture. The damaged lens tissue is removed by means of a vacuum tool resulting in total loss of vision to the affected patient. In order to restore normal or correctable vision, a variety of lens structures have been developed which are designed to be affixed in the intraocular space of the eye. Such structures commonly comprise a centrally positioned lens and a plurality of appendages attached to the lens which function to position and secure the lens in front of or just behind the pupil.

The artificial lens is formed from an optically clear substance and shaped so as to focus impinging light onto the retina of the eye. Such lenses are commonly optically formed to be plano-convex, convex-plano or bi-convex. The appendages attached to the lens typically comprise flexible legs of resilient plastic or metal fibers which are designed to make contact with appropriate structure in the interior of the eye.

One commonly employed type of intraocular lens structure is designed to position the lens in the anterior chamber of the eye just in front of the pupil. A structure of this type is disclosed, for example, by Kelman (U.S. Pat. No. 4,451,938). Another commonly employed type of intraocular lens structure is designed to position the lens in the posterior chamber of the eye just in back of the pupil. Devices of this type are disclosed by Faulkner (U.S. Pat. No. 4,366,582) and Shearing (U.S. Pat. No. 4,159,546). Streck (U.S. Pat. No. 4,361,913) discloses a lens which is indicated for possible use in either the anterior or posterior chambers.

Each of the structures mentioned above, except that of Kelman, is comprised of a single element lens with a plurality of haptics or position-fixation members attached to the lens. The lenses ordinarily have a circular perimeter. Thus, the incision in the cornea of the eye must be at least as long as the diameter of the lens. It is clear that the longer the incision, the greater will be the trauma to the eye and the longer will be the recovery time. Furthermore, since cataract surgery is usually performed on older patients, the general health of the patient may make it exceedingly important to keep the incision as short as possible. With this in mind, Kelman discloses in U.S. Pat. No. 4,451,938 an intraocular lens which is separable into two body portions. Each body portion is inserted separately through the cornea and the lens is then reassembled inside the eye during implacement. Such lens structure certainly leads to the necessity for a shorter incision in the cornea than would otherwise be the case. The Kelman device, however, leads to delicate manipulation of the parts within the eye in order to reassemble the intraocular lens. Furthermore, there is a possibility that the mating line of the two halves of the lens will cause distortion and other vision problems in the center of the field of view of the patient. The present invention addresses the problem of keeping the incision as short as possible in another way.

SUMMARY OF THE INVENTION

The present invention is directed to an intraocular lens having a lens body with a primary portion and a secondary portion, wherein the secondary portion may be folded with respect to the primary portion. In this way, the lens body may be manipulated from an implanted or operational configuration to a smaller insertion configuration so that the lens may be inserted through a smaller cut in the cornea than would otherwise be possible. A plurality of position-fixation members are attached to the lens body for holding the lens body in place relative to the eye.

In a preferred embodiment, the lens body has a pair of side secondary portions which are formed by separations between the primary portion and the secondary portions along chords of the preferable circular perimeter of the lens body. The chords are generally parallel to one another so that each secondary portion is on an opposite side of the main portion of the lens body. A connect member forms the attaching element between each secondary portion and the primary portion of the lens. The connect member has an outer edge which forms a part of the perimeter or circumference of the lens body. There is a slot between the connect member and the primary portion of the lens. The slot allows the connect member to bend inwardly so that the secondary portion may be moved on top of or beneath the primary portion and within an envelope formed by the perimeter of the primary portion. Just as there are opposite secondary portions, there are also opposite connect members. In addition, a pair of haptics or position-fixation members are attached to the primary portion of the lens in the region where the connect members attach to the primary portion. Opposing haptics hold the lens in place when implanted in either the anterior or posterior chambers of the eye.

In an alternate embodiment, the connect member includes a portion parallel to the axis of the lens and a portion perpendicular to the axis of the lens such that the secondary portions of the lens body are held beneath or outwardly on one side from the primary portion. With this embodiment, the secondary portions are easily compressed behind or, in other words, along the one side of the primary portion. Since the secondary portions are not present to perform a refractive function, but rather to perform a shading function, diplacing the secondary portions axially to one side from the primary portion does not detract from their intended function.

The present intraocular lens is particularly advantageous since the secondary portions may be folded inside the envelope of the perimeter of the primary portion of the lens so that during insertion, the lens may be snaked through a shorter cut in the cornea than would be possible if the lens were in its operational configuration represented by a circular perimeter.

The present invention is also advantageous in that the smaller insertion configuration is obtained with a lens which keeps the central portion of the lens always intact. Furthermore, the secondary portions are not missing, but are simply foldable between insertion and operational configurations so that when implanted, the side portions are present to shade the retina from direct rays of light at the edges of the pupillary opening. Although such rays of light are not needed for focusing the images observed by the patient, unless such rays are shaded, they irritate and are otherwise troublesome. Thus, the present invention provides for a way to insert a lens through a cut smaller than the diameter of a circular lens, but does so without giving up the benefits of a circular device.

It is further advantageous that the connect members between the secondary portions and the primary portion of the lens body are resilient so that when the secondary portions are released after insertion, they automatically assume a proper operational position.

The present invention is still further important because in spite of movable side portions and connect members along the outer perimeter of the primary portion of the lens, a region is still available for attachment of a pair of haptics on opposite sides of the lens. Furthermore, the haptics are designed to be yieldable and flexible and provide more than point contact on each side of the eye.

These several advantages and objects obtained by this invention are explained further hereinafter and, consequently, may be better understood by reference to the following drawings and descriptive matter wherein a preferred embodiment of the invention is illustrated and described in detail.

BRIEF DESCRIPTION OF THE DRAWINGS

FIG. 6 shows a dotted line and solid line top view of the folded lens as held by a tweezers illustrating two different positions during insertion and also shows in dotted line representative, implantation configuration relative to the eye structure;

FIG. 7 is a side elevational view of the lens, relative to a cross-sectional view of an eye, with the lens implanted in the posterior chamber;

DETAILED DESCRIPTION OF THE PREFERRED EMBODIMENT

Figure 1:
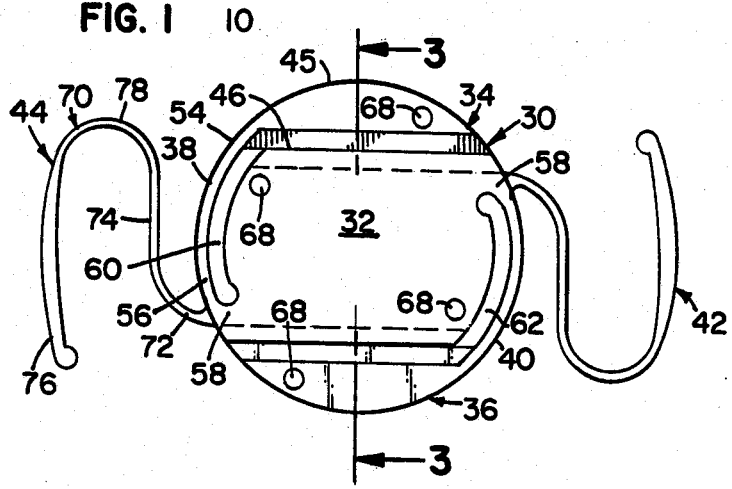
FIG. 1 is a top, plan view of an intraocular lens in accordance with the present invention.

Referring now to the drawings wherein like reference numerals designate identical or corresponding parts throughout the several views, and more particularly to FIG. 7, an intraocular lens in accordance with the present invention is designated generally by the numeral 10. Lens 10 is shown after implantation in a representative eye 12.

FIGS. 6 and 7 show simplified illustrations of the eye wherein portions not believed to be necessary to an understanding of the invention have been omitted for the sake of clarity. As shown in FIG. 7, the eyeball includes a cornea 14 having a scleral spur 16 near the base of the cornea. The diaphragm of iris 18 extends outwardly from the sides of the eyeball to define a pupillary or irial opening 20. The scleral spur 16 is spaced from the iris near the base of the cornea to define a groove 22. The natural lens has been removed with only the rear portion of the capsular bag 24 remaining. An aqueous zone between the cornea 14 and the capsular bag 24 is subdivided by the iris 18 into an anterior chamber 26 and a posterior chamber 28. Artificial lens 10 is shown installed in posterior chamber 28. It is understood that lens 10 may be implanted in either the anterior or posterior of chambers 26 or 28.

Figure 2:
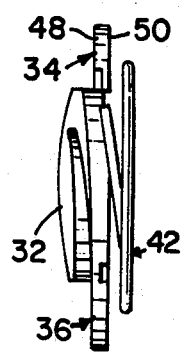
FIG. 2 is an end, elevational view of the lens of FIG. 1.
Figure 3:
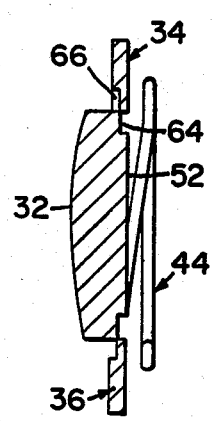
FIG. 3 is a cross-sectional view, taken along line 3—3 of FIG. 1.

As shown in FIGS. 1-3, intraocular lens 10 in accordance with the preferred embodiment of the present invention includes lens body 30 having a primary portion 32 and a pair of secondary portions 34 and 36. Lens 10 can be formed from any suitable material which is compatible with the environment of the eyeball, such as a non-toxic plastic, for example, polymethylmethacrylate. Secondary portions 34 and 36 are connected to primary portion 32 by a pair of connect members 38 and 40. Haptics or position-fixation members 42 and 44 extend from primary portion 32 outwardly for yieldingly pressing against the side of the eye at either the soft tissue at the edge of the capsular bag behind the iris in the posterior chamber or in groove 22 in the anterior chamber.

Figure 4:
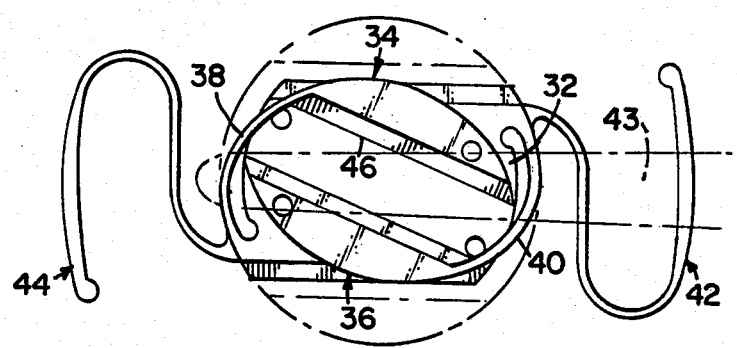
FIG. 4 is a top view of the lens of FIG. 1 when the secondary portions are folded.

Lens body 30 is preferably shaped to have a circular perimeter when connect members 38 and 40 are relaxed. As shown in FIG. 4, the insertion width of lens body 30 with connect members 38 and 40 bent is significantly smaller. Primary portion 32 forms the central refractive part of lens body 30. Secondary portions 34 and 36 form opposite sides of lens body 30 and are separated from primary portion 32 along substantially parallel chord lines. Thus, each of secondary portions 34 and 36 preferably have a portion of the circular circumference of lens body 30 as one edge 45 and a chord line as the other edge 46 as shown with respect to secondary portion 34 in FIG. 1. Although secondary portions 34 and 36 may mate with the curved or planar top and bottom surfaces of primary portion 32, it is only necessary that the top and bottom surfaces 48 and 50 of secondary portions 34 and 36 be planar. This is the case since the greatest percentage of light rays which are focused on the retina pass through primary portion 32. Although some light passes through secondary portions 34 and 36, which may be opaque, such light need not be focused to provide adequate vision. It has been found, however, that secondary portions 34 and 36, which may be opaque, should not be eliminated in an attempt to obtain a smaller lens body for insertion through the cornea since they serve the valuable purpose of shading the retina from side rays of light, which side rays otherwise irritate the retina.

Connect members 38 and 40 extend along the edge of primary portion 32 to secondary portions 34 and 36. As shown for connect member 38, for example, one end 54 of connect member 38 is attached preferably integrally at one end of secondary portion 34. The other end 56 is attached preferably integrally with primary portion 32. End 56 is attached to primary portion 32 at a region 58 which is a part of primary portion 32 and adjacent to the other secondary portion 36. The other connect member 40 is connected in a similar fashion and attached to primary portion 32 in a similar region at the other end of a diameter across lens body 30. Slots 60 and 62 separate connect members 38 and 40 from primary portion 32. Slots 60 and 62 provide space within which connect members 38 and 40 may bend as secondary portions 34 and 36 are folded under primary portion 32 to form the second perimeter for insertion as shown in FIG. 4. Since connect members 38 and 40 are preferably integral both with primary portion 32 and secondary portion 34 or 36, connect member 38, for example, has the thickness of primary portion 32 at end 56 while decreasing gradually in thickness to the thickness of secondary portion 34 at end 54 as shown in FIG. 2. Also, note that the outer edges of connect members 38 and 40 are a part of the circumferential perimeter of lens body 30.

Although not shown, secondary portions 34 and 36 may be separated from primary portion 32 by an axially aligned slot. Preferably, however, the separation is made in a way which creates as small a space as possible between secondary portions 34 and 36 and primary portion 32. As shown in FIG. 3, grooves 64 may be formed in back 52 of primary portion 32 near edges 46. Grooves 64 have a depth approximately one-half the thickness of secondary portions 34 and 36. Grooves 66 are formed adjacent to edges 46 in top surfaces 48 of secondary portions 34 and 36. Grooves 66 also have a depth of approximately one-half the thickness of secondary portions 34 and 36. In any case, grooves 64 and 66 have depths just sufficient so that preferably a corner of one of grooves 64 intersects a corner of one of grooves 66. With a wall of one of each of grooves 64 and 66 in common, the intersection corner provides a separation space between a secondary portion 34 or 36 and primary portion 32 wherein the separation space has as small a thickness as possible.

A plurality of openings 68 are formed in secondary portions 34 and 36 and primary portion 32 so that an appropriate instrument may engage one or more of the openings for the purpose of positioning lens 10 during implantation. Preferably, an opening 68 is formed near the end of each of secondary portions 34 and 36 and in a pair of opposite corners of primary portion 32 at opposite ends of edges 46 from openings 68 in secondary portions 34 and 36.

Haptics or position-fixation members 42 and 44 are preferably integral with primary portion 32 and attached at regions 58. Haptics 44 and 42 are identical. Haptic 42, for example, has a U-shaped portion 70 with a connecting portion 72 extending from one leg 74 of U-portion 70. The other leg 76 is preferably formed to fit along an imaginary surface substantially concentric to the circular perimeter of lens body 30. Such shape allows for bending of haptic 40 not only in the region of connect portion 72 but also along other portions of U-shape 70, and especially near base 78. Haptic 40 serves to provide more than a point contact against the side tissue of eye 12. In this way, intraocular lens 10 need have only a pair of haptics, rather than a larger number. Furthermore, haptics 42 and 44 are flexible and yieldable and, consequently, provide an appropriate tight fit. Haptics 42 and 44 are formed to extend sidewardly and slightly beneath back side 52 of primary portion 32, as shown in FIG. 3.

Figure 5:
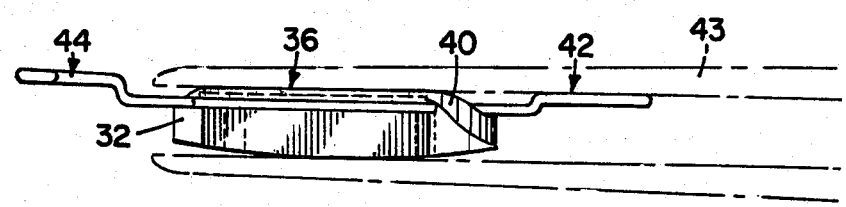
FIG. 5 is a side elevational view of the folded lens showing a tweezers in phantom lines holding the lens in the folded configuration.

As indicated hereinbefore, the present invention provides for a preferred circular first perimeter which is the desired shape after implantation of lens 10. In addition, the present invention provides for a reduced, second perimeter for insertion so that a smaller cut may be made in the cornea. The reduced second perimeter is shown in FIG. 4, wherein connect members 38 and 40 are bent so that secondary portions 34 and 36 fold behind primary portion 32 and within the envelope of the perimeter of primary portion 32. FIG. 5 shows a tweezer 43 or other tool in phantom lines holding the secondary portions 34 and 36 in the folded configuration. FIG. 6 shows one of the haptics being snaked through the cut in cornea 14 while the solid lines in FIG. 6 show lens 10 at a position where lens body 30 is ready to be inserted through the cut. Once inside the cornea, the tweezer or pinching tool may be released and secondary portions 34 and 36 automatically spring back to the operational configuration wherein connect members 38 and 40 are relaxed and lens body 30 again assumes a circular perimeter. FIG. 6 includes a further phantom illustration showing lens 10 relative to eye 14 after implantation.

Thus, in use, secondary portions 34 and 36 are folded with respect to primary portion 32 to form a folded configuration having a smaller perimeter than the unfolded configuration. The lens body is held in the folded configuration, and the intraocular lens is inserted through the incision in the cornea. The lens is positioned and secured to the eye with the position fixation members so that the lens body is in line with and substantially parallel with the pupillary or irial opening of the eye. The folded secondary portions 34 and 36 are then released for return to the unfolded configuration. The release of the folded secondary portions may also occur immediately after the lens has been inserted through the incision. A tool engages one or more of openings 68 so as to properly position lens 10.

In an alternate embodiment, as shown in FIGS. 8–11, the various elements which are similar to the earlier described embodiment are identified by identical numbers, only the numbers are primed. In this embodiment, lens 10' includes a lens body 30' having a primary portion 32' and a pair of secondary portions 34' and 36'. Secondary portions 34' and 36' are connected to primary portion 32' by a pair of connect members 38' and 40'. Haptics 42' and 44' extend outwardly from lens body 30'.

Figure 9:
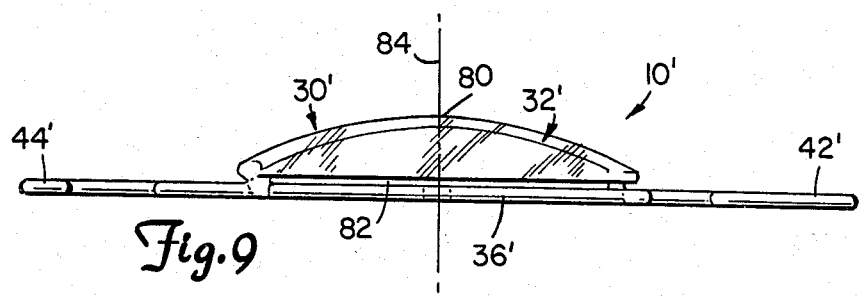
FIG. 9 is a side view of the lens of FIG. 8.
Figure 11:
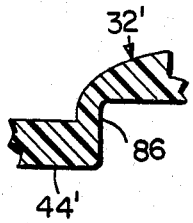
FIG. 11 is a cross-sectional view taken along line 11—11 of FIG. 8.
Figure 10:
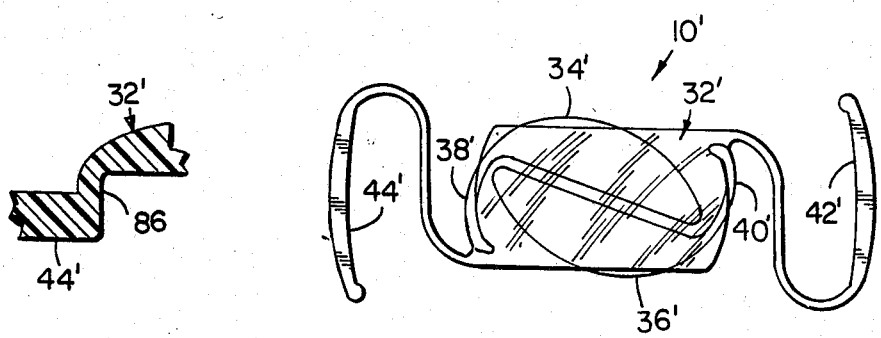
FIG. 10 is a top, plan view of the alternate embodiment showing the secondary portions folded toward one another.

Lens 10' is generally similar to lens 10. Lens 10' is different from lens 10 in that secondary portions 34' and 36', as well as haptics 42' and 44' are attached and held to primary portion 32' at a different side elevation. As shown in FIG. 9, primary portion 32' includes first and second opposite sides 80 and 82. Primary portion 32' has an axis 84. Side 82 of primary portion 32' is planar and is perpendicular to axis 84. It is understood, however, that primary portion 32' may be any type of lens, e.g., convex, concave, etc. In any case, connect members 38' and 40' and haptics 42' and 44' are held by a neck 86 (see FIG. 11) at a level spaced outwardly from a plane, in a direction along axis 84 opposite from first side 80, where the plane is perpendicular to axis 84 and is nearer second side 82 than side 80 and includes at least some of primary portion 32'. That is, in FIG. 9, the plane could be side 82 or at an elevational level spaced somewhat upwardly from side 82. Secondary portions 34' and 36' are held spaced from the plane at the same elevational level with respect to primary portion 32' as connect members 38' and 40'.

Figure 8:
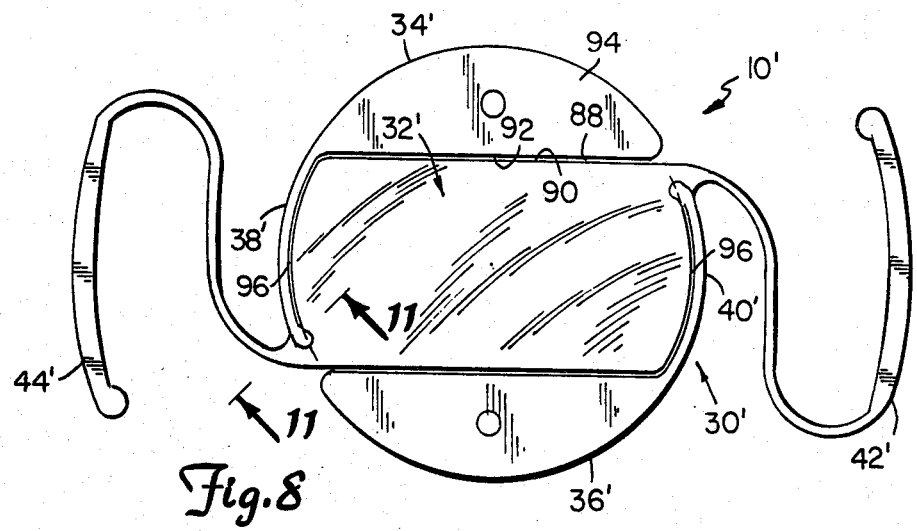
FIG. 8 is a top, plan view of an alternate embodiment of an intraocular lens in accordance with the present invention.

Neck 86 is connected to primary portion 32' at an end 96. Ends 96 are an edge of primary portion 32' which is not adjacent along most of its length to one of secondary portions 34' and 36'. In FIG. 8, one of necks 86 is located near a corner of one of ends 96 and one of edges 90 of primary portion 32'. The other neck 86 is located similarly at a diagonally opposite corner. Necks 86 extend in an axial direction sufficiently far so that when one of haptics 42' and 44' and one of connect members 38' and 40' connect to and extend away from neck 86, they do so in the relationship discussed hereinbefore.

Although necks 86 have been described with particularity and specifically located, it is understood that they could restructure and locate differently, or that the haptics and connect mambers be formed to angle axially in the same direction away from the primary portion in the fashion of haptics 42 and 44 as shown most clearly in FIGS. 2 and 3.

It is noted that since secondary portions 34' and 36' are present to provide a shading function, as opposed to a refractive function, it does not matter whether the secondary portions have an optically critical relationship with respect to primary portion 32'. The important realtionship concerns minimizing light from passing between primary portion 32' and secondary portions 34' and 36'. In this regard, in FIG. 8, secondary portions 34' and 36' are shown in a plan view as being slightly spaced from primary portion 32'. It is preferable, however, that a separation space 88 not occur between a first edge 90 of primary portion 32' and a second edge 92 of secondary portion 34', for example, but rather that space 88 would occur between a portion of a side 94 of secondary portion 34' and side 82 of primary portion 32'. It is understood, however, that space 88 may occur between first and second regions where the first region includes an edge 90 of primary portion 32' and adjacent parts of opposite sides 80 and 82 and where a second region includes an edge 92 and opposite sides 94 of secondary portion 34'.

Although the embodiments described have generally had a circular perimeter when viewed in plan view, it is understood that other shapes and configurations are encompassed within the spirit of the present invention. In particular, it is envisioned that both secondary portions could be attached to connecting members which have a common attachment to the primary portion at one of the ends of the primary portion, an end being an edge of the primary portion not adjacent to a secondary portion. This configuration would be particularly applicable with respect to the concept of the alternate embodiment wherein the secondary portions are held at a different elevational level than the primary portion.

In any case, the details of the structure and function, including advantages, have been set forth with respect to the preferred and an alternate embodiment of the present invention. It is understood, however, that such details are exemplary. Therefore, any changes made, especially in matters of shape, size, and arrangement, to the full extent extended by the general meaning of the terms in which the appended claims are expressed, are within the principle of the invention.

What is claimed is:

1. An intraocular lens for an eye, comprising:
   a lens body having a primary portion and a secondary portion, said primary portion and said secondary portion having adjacent surfaces, said lens body including a separation space between said adjacent surfaces;
   means for folding said secondary portion with respect to said primary portion, said folding means including a connect member unitary with and extending between said primary portion at a first location and said secondary portion at a second location, at least one of said first and second locations being spaced from said adjacent surfaces, said first and second locations being spaced with respect to one another, said connect member being yieldable so that said connect member will twist to fold said secondary portion with respect to said primary portion; and
   a plurality of position fixation members attached to said lens body;
   whereby said lens body may be folded from an operational configuration to a smaller insertion configuration thereby making implantation possible through a smaller cut in the cornea of the eye than would otherwise be possible.

2. An intraocular lens in accordance with claim 1 wherein said lens body has an axis and said primary portion has axially-spaced, opposite first and second sides, said folding means including means for holding said secondary portion axially spaced from the first side of said primary portion in a direction opposite from said second side.

3. An intraocular lens in accordance with claim 1 wherein said lens body includes a front side and a back side and opposite first edges, said primary portion including first grooves in one of the front side and back side along said first edges of said primary portion, said secondary portions including second edges and second grooves in the other of the front side and back side along said second edges, each of said first grooves cooperating with one of said second grooves to form said separation space between said primary portion and said secondary portions of said lens.

4. An intraocular lens for an eye, comprising:
   a lens body having a central primary portion and a pair of opposite side, secondary portions, said secondary portions being connected to said primary portion by yieldable connect members, said lens body having a first circular perimeter when said connect members are relaxed and said primary portion having a second perimeter, said secondary portions fitting within space the size of said second perimeter when said connect members are bent so as to fold said secondary portions over said primary portion, said lens body including slots between each of said connect members and said primary portion to allow said connect members to bend when said secondary portions are folded over said primary portion, each of said secondary portions being separated from said primary portion to form a separation space; and
   a plurality of position-fixation members attached to said primary portion, one of each of said position-fixation members and said connect members being attached in the same approximate region to said primary portion.

5. An intraocular lens in accordance with claim 4 wherein said primary portion includes first and second opposite sides, said primary portion also having an axis and a plane perpendicular to said axis, said plane being nearer said second side and including at least some of said primary portion, said connect members including means for holding said secondary portions outwardly from said plane in a direction along said axis opposite from said first side.

6. An intraocular lens for an eye, comprising:
a lens body having a central primary portion and a pair of opposite side, secondary portions, said primary portion having opposite first and second sides, said primary portion also having an axis and a plane perpendicular to said axis, said plane being nearer said first side and passing through at least some of said primary portion, said secondary portions being connected to said primary portion by connect members and at least one neck, said at least one neck extending generally axially, said connect members extending generally perpendicular to said axis, said lens body having a first perimeter when said connect members are relaxed and a second perimeter smaller than said first perimeter when said connect members are bent so as to fold said secondary portions substantially within an envelope defined by said primary portion when viewed axially, said connect members being spaced from said primary portion to allow said connect members to bend when said secondary portions are folded within the envelope of said primary portion, each of said secondary portions being separated from said primary portion; and
a plurality of position-fixation members attached to said primary portion for holding said lens relative to the eye.

* * * * *

UNITED STATES PATENT AND TRADEMARK OFFICE
CERTIFICATE OF CORRECTION

PATENT NO. : 4,664,665

DATED : May 12, 1987

INVENTOR(S) : Reuss et al

It is certified that error appears in the above-identified patent and that said Letters Patent are hereby corrected as shown below:

Column 8, line 6, after "member" insert --defining an arcuate slot with respect to said primary portion of the lens, said connect member being--.

Column 10, line 7, after "portion" insert --so as to define a slot--.

Signed and Sealed this

Twenty-sixth Day of April, 1988

Attest:

DONALD J. QUIGG

*Attesting Officer*        *Commissioner of Patents and Trademarks*